US00PP12119P2

(12) United States Plant Patent
Fransen

(10) Patent No.: US PP12,119 P2
(45) Date of Patent: Oct. 2, 2001

(54) HOSTA PLANT NAMED 'PARADISE JOYCE'

(75) Inventor: Marco Fransen, Ter Aar (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/642,383

(22) Filed: Aug. 22, 2000

(51) Int. Cl.[7] ..... A01H 5/00

(52) U.S. Cl. ..... Plt./353

(58) Field of Search ..... Plt./353

(56) References Cited

PUBLICATIONS

UPOV–ROM GTITM Computer Database, GTI JOUVE Retrieval Software, citations for 'Paradise Joyce' Feb. 2001.*

* cited by examiner

*Primary Examiner*—Bruce R. Campell
*Assistant Examiner*—Wendy C. Baker
(74) *Attorney, Agent, or Firm*—C. A. Whealy

(57) ABSTRACT

A distinct cultivar of Hosta plant named 'Paradise Joyce', characterized by its variegated leaf color; relatively compact plant habit; and light lavender-colored flowers that are positioned above the foliage on strong and erect scapes.

2 Drawing Sheets

BACKGROUND OF THE INVENTION

The present Invention relates to a new and distinct cultivar of Hosta plant, botanically known as Hosta hybrid, and hereinafter referred to by the culitvar name Paradise Joyce.

The new Hosta was discovered by the Inventor in a controlled environment in Ter Aar, The Netherlands, as a whole plant mutation of the Hosta hybrid cultivar Halcyon, not patented, in 1993. Plants of the cultivar Halcyon have solid blue-green-colored leaves whereas plants of the new Hosta have variegated leaves.

Asexual reproduction of the new cultivar by divisions harvested in Ter Aar, The Netherlands, has shown that the unique features of this new Hosta are stable and reproduced true to type in successive generations.

SUMMARY OF THE INVENTION

Plants of the cultivar Paradise Joyce have not been observed under all possible environmental conditions. The phenotype may vary somewhat with variations in environment such as temperature, light intensity, daylength, irrigation amount and frequency, and/or fertilizer rate without, however, any variance in genotype.

The following traits have been repeatedly observed and are determined to be the unique characteristics of 'Paradise Joyce'. These characteristics in combination distinguish 'Paradise Joyce' as a new and distinct cultivar:

1. Variegated leaf color.
2. Relatively compact plant habit.
3. Light lavender-colored flowers that are positioned above the foliage on strong and erect scapes.

Plants of the new Hosta can be compared to plants of the variegated Hosta hybrid June, not patented. Compared to plants of the new Hosta, plants of the cultivar June have darker and duller leaf colors.

BRIEF DESCRIPTION OF THE PHOTOGRAPHS

The accompanying colored photographs illustrate the overall appearance of the new Hosta, showing the colors as true as it is reasonably possible to obtain in colored reproductions of this type. Colors in the photographs may differ slightly from the color values cited in the detailed botanical description which more accurately describe the actual colors of the new Hosta.

The photograph on the first sheet comprises a side perspective view of typical flowering plants of 'Paradise Joyce' grown in containers.

The photograph at the top of the second sheet is a close-up view of typcal flowers of 'Paradise Joyce'.

The photograph at the bottom of the second sheet is a close-up view of the upper surface of a typical leaf of 'Paradise Joyce'.

DETAILED BOTANICAL DESCRIPTION

In the following description, color references are made to The Royal Horticultural Society Colour Chart except where general terms of ordinary dictionary significance are used. Plants used for the following description were about 40 weeks old and grown in 17-cm containers under field conditions which closely approximate commercial production conditions during the spring and summer in Ter Aar, The Netherlands.

Botanical classification: Hosta hybrid cultivar paradise Joyce.

Parentage: Whole plant mutation of Hosta hybrid cutlivar Halcyon, not patented.

Propagation:

*Type cutting.*—By divisions.

*Rooting time.*—Divisions harvested in the spring develop roots in about 30 days.

*Root description.*—Fleshy.

Plant description:

*Form.*—Perennial flowering plant; initially upright becoming outwardly arching as leaves develop; inverted triangle. Moderately clumping. Appropriate for 17-cm containers.

*Crop time.*—After rooting, about 40 weeks are required to produce finished flowering plants in 17-cm containers.

*Plant height.*—From soil level to top of leaf plane: About 20 cm. From soil level to top of flowering stems: About 45 cm.

*Plant diameter.*—About 40 cm.

*Vigor.*—Moderately vigorous.

*Foliage description.*—Leaves basal, simple, generally symmetrical, and long-persisting. Length: About 12 cm. Width: About 6.8 cm. Shape: Ovate. Apex: Acuminate to apiculate. Base: Rounded to cordate. Margin: Entire. Texture: Glabrous, dull. Petiole: Length: About 15 cm. Diameter: About 7 mm. Color: Young foliage, upper surface: Center, 144B; margins, 133B to 139B. Young foliage, lower surface: Center, 144B; margins, 136B; glaucous. Mature foliage, upper surface: Center, 144A to 2D; margins, 137A to 137B. Mature foliage, lower surface: Center, 145C; margins, 136B to 137B; glaucous. Petiole color: 145A to 145C.

Flower description:

*Appearance.*—Single campanulate flowers with fused perianth arranged on one-side racemes. Flowering stems arise from leaf axils. Typically two flowering stems per plant. Flowers not persistent.

*Quantity of flowers.*—About 20 flowers per raceme.

*Natural flowering season.*—Summer in The Netherlands; flowering continuous.

*Fragrance.*—Not fragrant.

*Flower longevity.*—About 4 to 7 days.

*Flower size.*—Length: About 6.5 cm. Diameter: About 1.5 cm.

*Flower buds* (*about days before opening*).—Length: About 3.4 cm. Diameter: About 9 mm. Shape: Oblanceolate. Color: 76B to 85C.

*Perianth.*—Arrangement: Three interior and three exterior tepals; fused. Tepal length: About 5 cm. Tepal width: About 8 mm. Tepal shape: Elongated; apex, acute; margin, entire. Tepal texture: Smooth; glabrous. Tepal color: When opening, upper and lower surfaces: 76C. Fully opened, upper and lower surfaces: 76D.

*Floral bracts.*—Arrangement: At pedicel base. Length: About 2.5 cm. Width: About 1.1 cm. Shape: Broadly lanceolate. Color: 145C to 145D.

*Pedicel.*—Length: About 5 mm. Angle: Erect to about 30° from vertical. Strength: Moderate to strong. Color: 76C.

*Scape.*—Length: About 45 cm. Aspect: Mostly upright. Texture: Smooth; glaucous. Color: 188A to 188B.

*Reproductive organs.*—Stamens: Quantity: Six; dorsifixed. Anther size: About 3 by 1 mm. Anther color: Dark purple blue. Pollen amount: Scarce. Pistils: Quantity: One. Pistil length: About 5 cm. Style length: About 4.8 cm. Style color: 150D. Stigma color: 157D. Ovary color: 145A.

*Seed description.*—Seed development has not been observed.

Disease resistance: Plants of the new Hosta have been noted to be somewhat resistant to pathogens common to Hosta.

It is claimed:

1. A new and distinct cultivar of Hosta plant named 'Paradise Joyce', as illustrated and described.

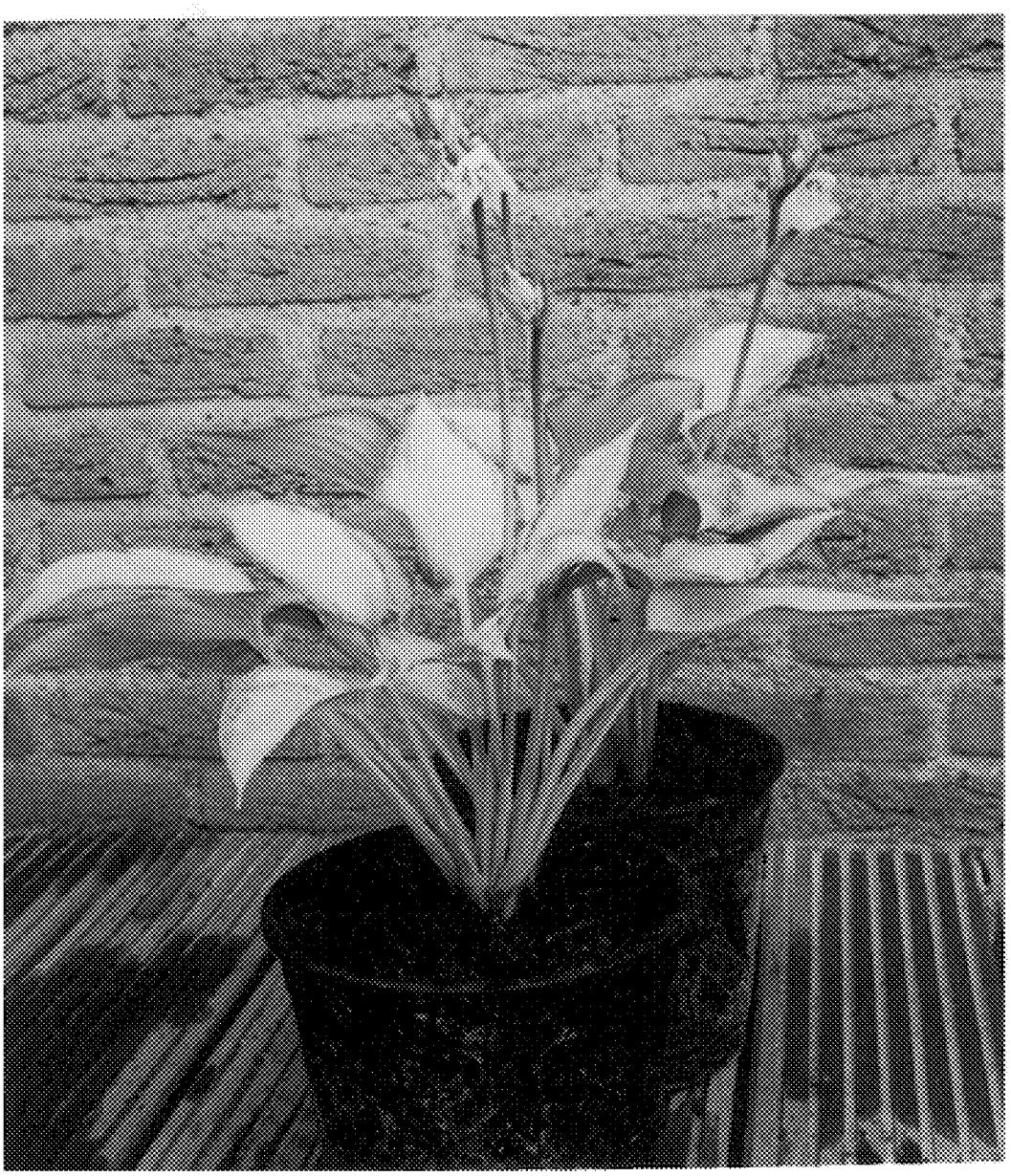

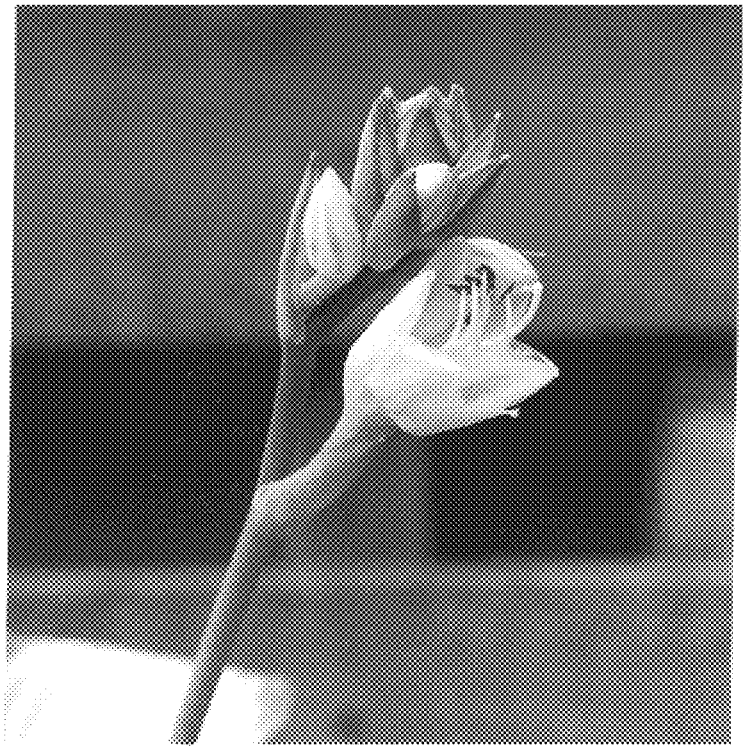
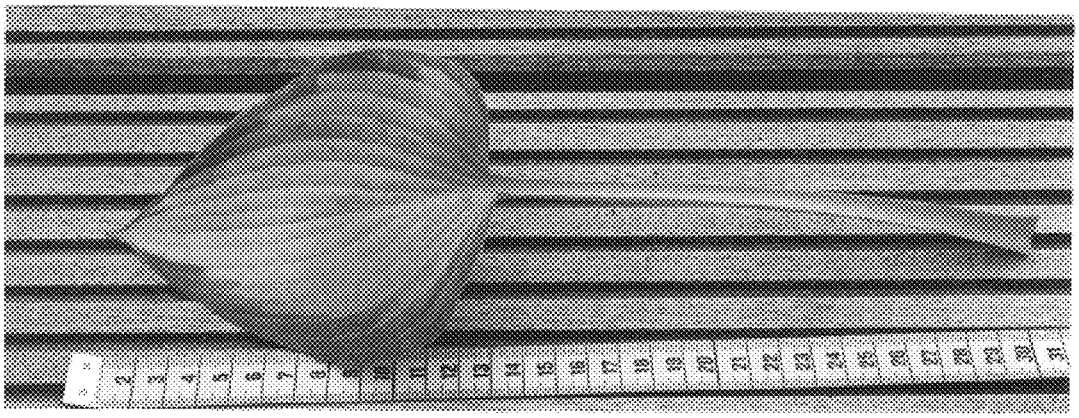

* * * * *